United States Patent
Wick

[11] Patent Number: 6,129,929
[45] Date of Patent: Oct. 10, 2000

[54] PATCH APPLICATOR

[75] Inventor: John Joachim Wick, Miami, Fla.

[73] Assignee: Noven Pharmaceuticals, Inc.

[21] Appl. No.: 09/182,654

[22] Filed: Oct. 30, 1998

[51] Int. Cl.[7] .................................................. A61F 13/02
[52] U.S. Cl. ........................... 424/448; 424/449; 602/58
[58] Field of Search .................... 424/449, 448, 424/402, 404

[56] References Cited

U.S. PATENT DOCUMENTS

| | | | |
|---|---|---|---|
| Re. 33,353 | 9/1990 | Heinecke | 428/40 |
| 2,579,403 | 12/1951 | Slomowitz et al. | 128/168 |
| 2,629,378 | 2/1953 | Barton | 128/268 |
| 2,969,057 | 1/1961 | Simmons | 128/2 |
| 3,120,229 | 2/1964 | Hinkamp | 128/156 |
| 3,888,247 | 6/1975 | Stenvall | 128/156 |
| 4,022,203 | 5/1977 | Ackley | 128/156 |
| 4,176,664 | 12/1979 | Kalish | 128/156 |
| 4,235,337 | 11/1980 | Dotta | 206/441 |
| 4,564,010 | 1/1986 | Coughlan et al. | 128/156 |
| 4,598,004 | 7/1986 | Heinecke | 428/40 |
| 4,600,001 | 7/1986 | Gilman | 128/156 |
| 4,638,043 | 1/1987 | Szycher et al. | 528/75 |
| 4,767,401 | 8/1988 | Seiderman | 604/20 |
| 4,832,008 | 5/1989 | Gilman | 128/155 |
| 4,832,009 | 5/1989 | Dillon | 128/156 |
| 4,911,707 | 3/1990 | Heiber et al. | 604/307 |
| 4,917,676 | 4/1990 | Heiber et al. | 424/449 |
| 4,926,850 | 5/1990 | Lott et al. | 128/155 |
| 4,928,680 | 5/1990 | Sandbank | 128/155 |
| 4,994,267 | 2/1991 | Sablorsky | 424/78 |
| 5,018,516 | 5/1991 | Gilman | 128/155 |
| 5,052,381 | 10/1991 | Gilbert et al. | 128/155 |
| 5,074,293 | 12/1991 | Lott et al. | 128/155 |
| 5,099,832 | 3/1992 | Ward | 602/57 |
| 5,160,315 | 11/1992 | Heinecke et al. | 602/57 |
| 5,275,284 | 1/1994 | Onotsky | 206/441 |
| 5,300,291 | 4/1994 | Sablotsky et al. | 424/78.18 |
| 5,336,162 | 8/1994 | Ota et al. | 602/41 |
| 5,397,297 | 3/1995 | Hunter | 602/54 |
| 5,415,626 | 5/1995 | Goodman et al. | 602/57 |
| 5,415,627 | 5/1995 | Rasmussen et al. | 602/57 |
| 5,417,674 | 5/1995 | Smith et al. | 604/289 |
| 5,423,737 | 6/1995 | Cartmell et al. | 602/57 |
| 5,437,622 | 8/1995 | Carion | 602/57 |
| 5,476,443 | 12/1995 | Cartmell et al. | 602/58 |
| 5,489,262 | 2/1996 | Cartmell et al. | 602/57 |
| 5,520,629 | 5/1996 | Heinecke et al. | 602/57 |
| 5,562,642 | 10/1996 | Smith et al. | 604/289 |
| 5,607,388 | 3/1997 | Ewall | 602/58 |
| 5,628,724 | 5/1997 | Debusk et al. | 602/58 |
| 5,709,651 | 1/1998 | Ward | 602/57 |
| 5,733,251 | 3/1998 | Johns | 602/57 |
| 5,755,681 | 5/1998 | Plews | 602/58 |
| 5,780,048 | 7/1998 | Lee | 424/443 |

*Primary Examiner*—Thurman K. Page
*Assistant Examiner*—Isis Ghali
*Attorney, Agent, or Firm*—Jay G. Kolman, Esq.; Oldham & Oldham Co., I.P.A.; Scott M. Oldham

[57] ABSTRACT

A patch applicator for easy application of a transdermal patch, especially a small transdermal patch of size 20 cm² or less. The patch applicator includes a bottom release liner, a transdermal patch releaseably attached to the bottom release liner, and a top release liner releasably attached to the transdermal patch. The top release liner has a first tab which extends beyond an end margin of the transdermal patch, so that a patch user may easily grasp the tab and remove the top release liner and patch from the lower release liner. The patch is then applied to the skin or mucosa A second tab of the top release liner preferably also extends beyond an end margin of the patch so that the top release liner may be easily removed from the patch after the patch has been applied to the skin or mucosa. Alternatively, the first and second tabs are removed from the patch by peeling back the tabs from a slit between the tabs. The first and second tabs are differently and distinctly marked to aid the patch user in applying the patch. The patch applicator reduces loss in manufacturing yield, and especially benefits the elderly population.

24 Claims, 3 Drawing Sheets

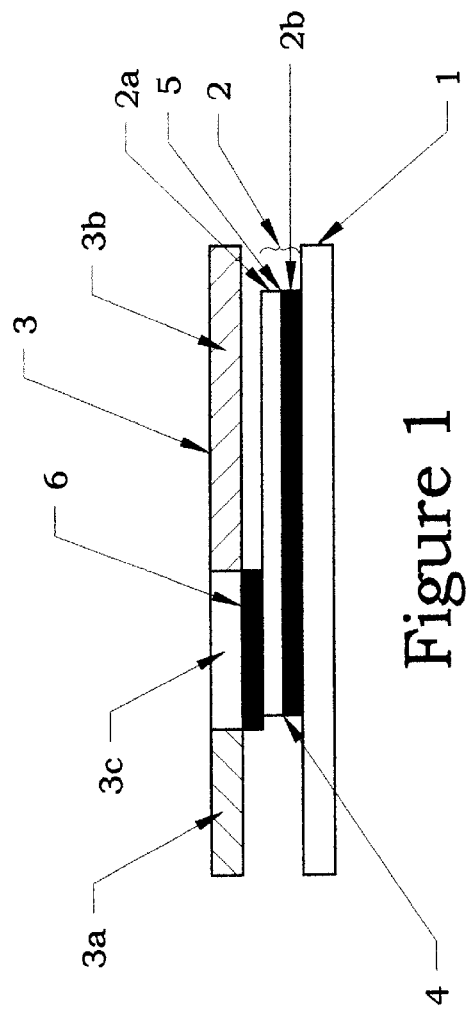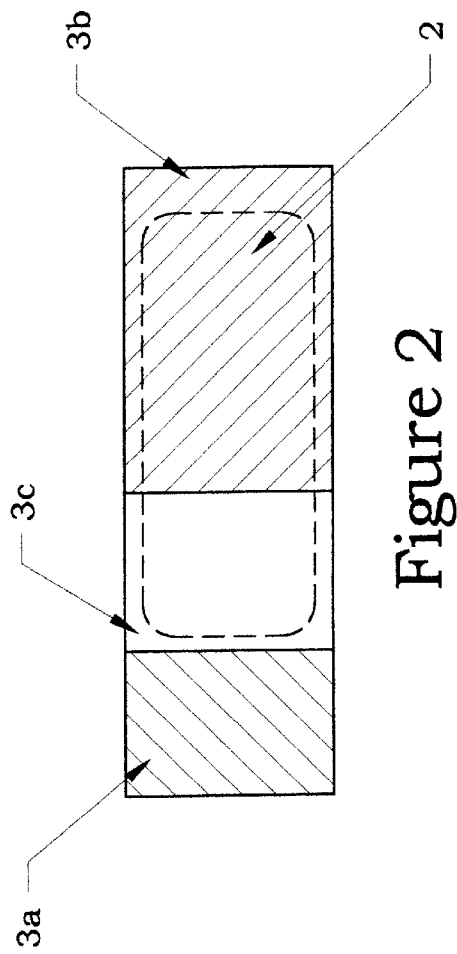

PATCH APPLICATOR

BACKGROUND OF THE INVENTION

This invention relates to a patch applicator system for a transdermal patch which facilitates the application of small transdermal patches.

A transdermal patch requires intimate contact with the site of application in order to effectively deliver a drug either locally or systemically. Such contact is usually achieved by means of some type of adhesive layer on the face of the patch. To protect the adhesive layer prior to application by the patch user, a releasable material is typically laminated to or applied over the adhesive which is then later removed and discarded before use. Removal of the release liner is often difficult without a method or means of "peeling" it away from the adhesive.

One method to accomplish this is by either partially cutting through the release liner ("scoring") or completely cutting through the release liner. Since transdermal patches are generally flexible, they can be bent enough to allow the scored release liner to be broken at the score and peeled back, provided the release liner is more rigid than the patch itself. When a more flexible release liner is used, it is preferable to cut completely through the release liner.

Whether the release liner is scored or cut completely through, precision equipment is required. In addition to having to continually monitor and maintain such equipment, production problems including cracking of the release liner and imperfect or improper depth of the scores or cuts (for example, cutting into the adhesive or entirely through the patch) can occur. And even when the release liner is scored or cut as desired, separation from the adhesive layer can still prove to be cumbersome and difficult.

Improvements in transdermal drug delivery technology such as those described in U.S. Pat. Nos. 5,474,783 and 5,656,286 both assigned to Noven Pharmaceuticals, Inc., Miami, Fla., have resulted in the ability to produce smaller and smaller patches without compromising the ability to deliver a therapeutically effective amount of the drug. Smaller patches, those less than 20 $cm^2$ in surface area, and especially those less than 10 $cm^2$, provide many advantages over larger patches.

The larger the patch, the greater the tendency of the patch to wrinkle, fold, become loose and dislodge from the application site, all of which reduces its ability to effectively deliver a therapeutic amount of drug. Larger patches, due to their size, offer limited areas on a body for application and are often uncomfortable to wear as well as potentially being unsightly. Since larger patches are more likely to be seen on an individual, the patch user may become more self-conscious even embarrassed. Costs to produce larger patches are obviously greater due to the need for greater amounts of drug, adhesives, excipients and additives, which in turn increases the risks of irritation and sensitization especially since the application sites are reduced. Larger patches are more cumbersome to apply, adhering to itself or another inappropriate surface such as the fingers of the patch user, once the release liner is removed.

While smaller size patches offer numerous advantages over its larger counterparts, the use of conventional scoring and cutting methods for the release liner creates greater disadvantages. As the size of the patch is reduced, the area that may be grasped when peeling the release liner away is also reduced. Conversely, this increases the area of the patch which is touched before application, which can result in loss of adhesivity before application. Touching the adhesive also increases risk of contamination to both the application site as well as the sensitive areas of the user, such as the eyes or mouth, if touched by the user after application. Certain segments of the population, such as the elderly or those with arthritic conditions, may further find handling of smaller patches difficult. In view of the foregoing, it will be appreciated that providing a more efficient and easily removable release liner would be an advancement in the art.

SUMMARY OF THE INVENTION

It is an object of an embodiment of this invention to provide a transdermal patch whose release liner is more easily removable and without wrinkling the transdermal patch.

It is a further object of an embodiment of this invention to provide a means to easily remove the release liner and apply the patch with only one hand.

It is another object of an embodiment of this invention to provide a transdermal system which reduces the problem of touching the adhesive layer when removing the release liner.

An embodiment of the present invention overcomes the problems of the prior art by providing a transdermal patch applicator where the transdermal patch is especially easy to remove. In this embodiment the patch has a temporary upper release liner which is large enough to include a handling tab or tabs which aids in removing the transdermal patch from the underlying lower release liner and aids in applying the patch to a desired area of the skin or mucosa. A portion of the tab or tabs extend out beyond the margin of the transdermal patch. The transdermal patch is releasably affixed to the lower release liner, while the upper release liner is releasably affixed to the transdermal patch.

In one embodiment of the invention, the upper release liner has a central region between first and second tabs. In this embodiment the second tab extends partially over the transdermal patch and partially beyond an end margin of the patch. At least a portion of the first tab also extends beyond an end margin of the transdermal patch. An adhesive contacts the transdermal patch and the central region of the upper release liner, but does not contact either the first or second tab. The first and second tabs are of different colors, or otherwise identified to aid in application of the patch.

In a second embodiment of the invention, the top release liner has a first tab and a second tab where at least a portion of the first tab extends beyond an end margin of the transdermal patch. In this embodiment the first and second tabs are separated by a slit. In applying the transdermal patch in this embodiment, the first tab is grasped, and the transdermal patch is lifted from the lower release liner. The transdermal patch is then applied to a skin or mucosa region. Finally, the first and second tabs are then removed from the transdermal patch by peeling back the tabs at the slit.

Further features will become more fully apparent in the following description of the embodiments of this invention and from the appended claims.

BRIEF DESCRIPTION OF THE DRAWINGS

FIG. 1 is a side view of a first embodiment of the invention.

FIG. 2 is a top view of the first embodiment of the invention.

DETAILED DESCRIPTION OF THE PREFERRED EMBODIMENTS

Figure 3:
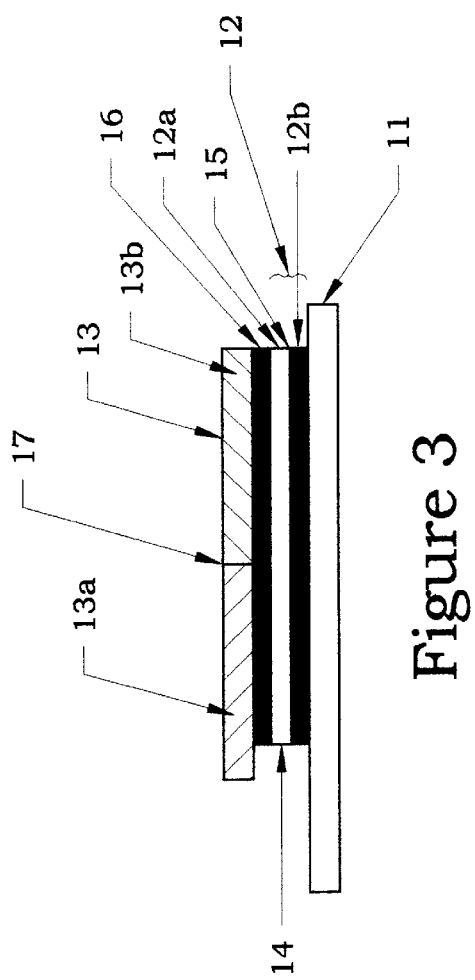
FIG. 3 is a side view of a second embodiment of the invention.

FIGS. 1 and 2 illustrate a first embodiment of the invention. Transdermal patch 2 is releasably attached to an underlying bottom release liner 1. Patch 2 comprises a patch adhesive layer 2b which contacts the underlying bottom release liner 1 on one side, and which is applied to the skin or mucosa of the patch user after removal of the release liner 1, and backing layer 2a on the other side. Typically, the patch adhesive layer 2b serves as the carrier for the drug or drugs to be administered to the patch user. Alternatively, additional layers (not shown) may be included between the patch adhesive layer 2b and the backing layer 2a, which layers may or may not also be adhesives or incorporate one or more drugs, and include any of the non-toxic polymers well known in the art used to carry drugs or act as rate-controlling membranes. Patch adhesive layer 2b is preferably a continuous layer, but may be discontinuous as long as the drug may be administered as is necessary to effect therapy.

Suitable adhesives for use as the patch adhesive layer are intended in their broadest sense to mean any natural or synthetic polymer that is capable of sticking to the site of application, and include bioadhesives (also referred to a mucoadhesives) and pressure-sensitive adhesives as are generally known in the art. A polymer is an adhesive within the meaning of the term if it has the properties of an adhesive per se or if it functions as an adhesive by the addition of tackifiers, plasticizers, cross-linking agents or other additives. Especially preferred adhesives are acrylics, vinyl acetates, natural and synthetic rubbers, natural and synthetic gums, polysiloxanes, polyacrylates, ethylene/vinyl acetate copolymers, polyvinylpyrrolidones, vinylpyrrolidone copolymers and particularly vinyl pyrrolidone/vinylacetates, styrene block copolymers, and mixtures thereof. Particularly suitable bioadhesives or mucoadhesives include natural or synthetic polysaccharides and polyacrylic acid polymers, and mixtures thereof. The term "polysaccharide" as used herein means a carbohydrate decomposable by hydrolysis into two or more molecules of monosaccharide or their drivatives. Preferred polyscaccharides include cellulose materials and natural gums. Such adhesives may be used singularly, or in blends of two or more.

The layers of transdermal patch 2, other than the backing layer 2a, can also contain agents known to accelerate the delivery of a drug through the skin or mucosa. These agents have been referred to as skin-penetration enhancers, accelerants, adjuvants, and sorption promoters, and are herein referred to collectively as "enhancers." This class of agents includes those with diverse mechanisms of action including those which have the function of improving the solubility and diffusibility of a drug within the multiple polymer and those which improve percutaneous adsorption, for example, by changing the ability of the stratum corneum to retain moisture, softening the skin, improving the skin's or mucosa's permeability, acting as penetration assistants or hair-follicle openers or changing the state of the skin or mucosa including the boundary layer. Some of these agents have more than one mechanism of action, but in essence they serve to enhance the delivery of a drug.

In addition to enhancers, there may also be incorporated various pharmaceutically acceptable additives and excipients available to those skilled in the art. These additives include tackifying agents such as aliphatic hydrocarbons, mixed aliphatic and aromatic hydrocarbons, aromatic hydrocarbons, substituted aromatic hydrocarbons, hydrogenated esters, polyterpenses and hydrogenated wood rosins; binders such as lecithin which "bind" the other ingredients; rheological agents (thickeners) containing silicone such as fumed silica, reagent grade sand, precipitated silica, amorphous silica, colloidal silicon dioxide, fused silica, silica gel, quartz and particulate siliceous materials commercially available as Syloid®, Cabosil®, Aerosil® and Whitelite®, for purposes of enhancing the uniform consistency or continuous phase of the final composition; and other additives and excipients such as diluents, stabilizers, fillers, clays, buffering agents, biocides, humectants, antiirritants, antioxidants, preservatives, flavoring agents, colorants, pigments and the like.

Illustrative examples of suitable adhesives, enhancers and other additives and excipients are described in U.S. Pat. Nos. 5,474,783, and 5,656,386 both assigned to Noven Pharmaceuticals, Inc., Miami, Fla., and are incorporated herein by reference.

As used herein, the term "drug" is intended to have its broadest interpretation as any therapeutically, prophylactically, pharmacologically or physiologically beneficial active substance, or mixture thereof, which is delivered to a living organism to produce a desired, usually beneficial, effect. More specifically, any substance which is capable of producing a pharmacological response, localized or systemic, irrespective of whether therapeutic, diagnostic, or prophylactic in nature, in animals is within the contemplation of the term. Also within the contemplation of the term are such agents as insect repellents, sun screens, cosmetic agents, etc. It should be noted that the drugs may be used singly or as a mixture of two or more such agents, and in amounts sufficient to prevent, cure, diagnose or treat a disease or other condition, as the case may be.

The backing layer 2a is typically occlusive to water permeation, serves to retain and maintain the patch adhesive layer 2b disposed thereon in a defined size and shape, prevent loss of the drug and/or enhancers to the environment, render the patch (in conjunction with the release liner) transportable, and generally provides protection both prior to and after application of the patch to the user.

Suitable materials that can be used singularly or in combination, as laminates or as coextrusions, to form the backing layer are well known in the art and include films or sheets of polyethylene, polyester, polypropylene, polyurethane, polyolefin, polyvinyl alcohol, polyvinyl chloride, polyvinylidene, polyamide, vinyl acetate resins, BAREX®, ethylene/vinyl acetate copolymers, ethylene/ethylacrylate copolymers, metal-vapor deposited films or sheets thereof, rubber sheets or films, expanded synthetic resin sheets or films, non-woven fabrics, fabrics, knitted fabrics, clothes, foils and papers. If a thermoplastic resin is used, such as polyurethene, polyamide, polyethylene, polyvinyl chloride, polycarbonate, polystyrene or polyvinylidne resin, then a top releaser liner (described below) may be thermobonded to the backing layer 2a.

The backing layer generally has a thickness in the range of 2 to 1000 micrometers. The backing layer may be pigmented, for example colored to either match with or conversely easily distinguish from the site of application, and/or contain printing, labeling and other means of identification and/or tracability of the patch itself. The backing layer may further be made opaque or substantially opaque (i.e., preventing light or certain energy wavelengths from penetrating or passing through), such as by metallization, fillers, inks, dyes and the like, for purposes of protecting photosensitive active agents from degradation and/or preventing photoallergic reactions or irritations on the subject.

The bottom release liner 1 is also intended to prevent loss of the drug and/or enhancers to the environment, and render the individual patch (in conjunction with the backing layer) transportable, as well as generally protect the patch from contamination and the like until its application by the user. The release liner is typically also impermeable and occlusive, and must be compatible with the particular adhesives and/or drugs so as not to interfere with their ultimate application and therapeutic effect.

Suitable materials that can be used singularly or in combination, as laminates or as coextrusions, to form the release liner are also well known in the art, for example cellophane, nylon, glassine paper, acrilonitride or acrylic copolymers, and include any material suitable for use as the backing layer. When the release liner is composed of a material which typically does not readily release (i.e., is not easily removed or separated from the patch adhesive layer), for example paper, a coating material such as a silicone, teflon or thermoplastic materials such as polyester, polyvinyl resin, polyethylene or cellulose acetate, may be applied to the release liner by any conventional means. Preferred release liners are films commercially available from DuPont, Wilmington, Del., under the trademark Mylar®, and fluropolymer and silicone coated films commercially available from Rexam Release, Oak Brook, Ill. under the trademark FL2000® and MRL2000, and from 3M Corporation, St. Paul, Minn. under the trademark ScotchPak® 1022.

The top release liner 3 is releasably attached to the underlying transdermal patch 2. In this embodiment, the top release liner 3 has three regions, 3a, 3b, and 3c. The central region 3c may be attached to the underlying backing layer 2a by means of an adhesive layer 6. Alternatively, the top release liner 3 may be thermobonded or fusion bonded directly to the backing layer 2a. The top release liner 3 also has a first tab 3a which extends beyond a first end margin 4 of the transdermal patch 2. The first tab 3a may be easily grasped and allows easy removal of the top release liner and patch 2 from the bottom release liner 1. In that regard, it is preferred that there be adhesive only between the central region 3c and the patch 2. It is also preferred that the first tab 3a extend only over the bottom release liner 1 and not the patch 2, so that the first tab 3a may be more easily grasped. However, the first tab 3a may extend partially over the patch 2, and there may be adhesive between the first tab 3a and the patch 2 as long as the easy grasping of the first tab 3a is not overly restricted. If the top release liner 3 is thermobonded or fusion bonded to the backing layer 2a, then preferably only the central region 3c of the top release liner 3 is bonded to the backing layer 2a.

The top release liner 3 also has a second tab 3b which extends partially over the patch 2 and partially beyond a second end margin 5 of the patch 2. After the patch 2 and top release liner 3 are removed from the lower release liner 1 and applied to the skin or mucosa, the second tab 3b is grasped and the top release liner 3 is peeled from the patch 2 which remains on the skin or mucosa. In order to facilitate the easiest removal of the top release liner from the patch, it is preferred that there be no adhesive between the second tab 3b and the patch 2. However, there may be some adhesive between the second tab 3b and the patch 2, as long as the easy grasping of the second tab 3b is not overly restricted.

The three regions of the top release liner may be made of a single material. For instance, the top release liner may be made of material similar to the bottom release liner, such as silicone coated release paper, glassine paper, polyester, polyvinyl resin, polyethylene, and other materials known to be appropriate for a release liner. The top release liner may also be a laminate of materials, in a similar fashion to the bottom release liner, such as aluminum foil coated with a thermoplastic material. Alternatively, the three regions of the top release liner may be formed of different materials, or of a single material with a different thickness for the three regions.

The three regions of the top release liner are marked to identify the regions and thereby aid in applying the transdermal patch. The first tab 3a is marked with a first identifying indicia and the second tab 3b is marked with a second identifying indicia. The first identifying indicia is different and distinct from the second identifying indicia so that a patch user will understand that the first tab 3a is to be grasped first when removing the patch from the underlying bottom release liner. The first and second tabs may be identified and distinguished by a variety of means including color, printing, labeling, transparity/opaqueness of the materials, or any combination thereof. For example, the first and second tabs may be marked with the numbers 1 and 2, respectively, indicating that the first tab 3a is to be grasped first. The first tab 3a may also be formed of a different and/or thicker material than the second tab 3b as an indication that the first tab is to be grasped first. The patch applicator may be accompanied by instructions indicating which of the tabs is the first tab, and detailing how the patch is to be applied. Alternatively, the instructions may be on the tabs themselves. For example, the first tab may be marked "Pull first" and the second tab may be marked "Pull second".

The adhesive layer 6 is made of any material suitable for releasably attaching the top release liner 3 to the backing layer 2a. Suitable adhesives include polyvinyl chloride, and polyvinyl acetate. Alternatively, if thermoplastics are used for the top release liner 3 and backing layer 2a, the top release liner 3 may be attached to the backing layer 2a by thermobonding or fusion bonding, and the adhesive layer 6 may be omitted. It is desirable that the stripping load of the top release liner 3 from the backing layer 2a is equal to or greater than the stripping load of the bottom release liner 1 from the patch 2. If the stripping load of the top release liner 3 is less, the top release liner may undesirably peel before the bottom release liner 1 is removed. Accordingly, the ratio of the stripping load of the top release liner 3 from the backing layer to the stripping load of the bottom release liner 1 from the patch is set to greater than or equal to 1.0. This may be accomplished by ensuring that the peel strength of adhesive 6 is greater than that of the patch adhesive 2b, or by forming the patch adhesive in a discontinuous fashion to decrease the adhesion between the patch and the underlying bottom release liner, or by a combination. Preferably, adhesive layer 6 extends to a point directly above or slightly beyond the first end margin 4. This will decrease the risk that the top release liner 3 will peel from the patch 2 when removing the patch from the bottom release liner 1.

A method of removing the patch 2 from the bottom release liner 1 and applying it to the skin or mucosa is as follows. The first end tab 3a is grasped between the thumb and forefinger of one hand, while the other hand grasps the lower release liner 1. The first end tab 3a is then pulled, releasing the patch 2 along with the top release liner 3 from the bottom release liner 1. After the bottom release liner 1 is removed and discarded, the patch is positioned on the skin or mucosa where it adhesively attaches. The second end tab 3b is grasped between the thumb and forefinger of one hand. The second end tab 3b is then pulled, thereby peeling back and removing the top release liner 3 from the transdermal patch 2.

Figure 4:
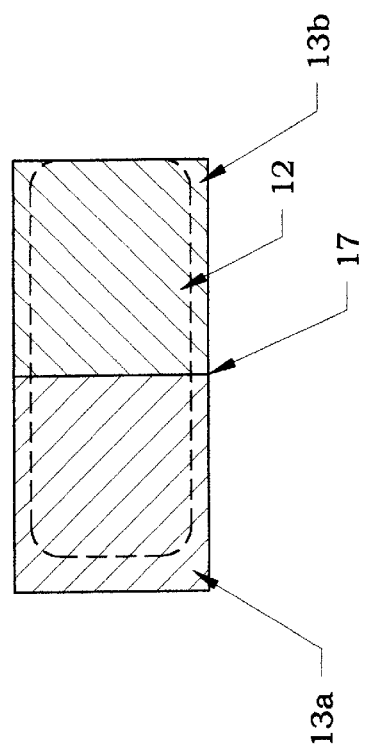
FIG. 4 is a top view of the second embodiment of the invention.

FIGS. 3 and 4 illustrate a second embodiment of the invention. The second embodiment is similar to the first embodiment. However, in the second embodiment the top release liner is removed from the patch by peeling back two separate regions of the top release liner separated by a slit, instead of by pulling back on a tab extending beyond the end margin of the patch. The first embodiment is currently more preferred than the second embodiment, because the top release liner 3 in the first embodiment is more easily removed, and because there is less chance of touching adhesive when applying the patch of the first embodiment, as compared to the second embodiment patch.

In the second embodiment, a transdermal patch 12 is releasably attached to a bottom release liner 11. As with the first embodiment, the transdermal patch 12 may be releasably attached by including a patch adhesive 12b in the patch 12, or an additional adhesive layer (not shown) may be included between the bottom release liner 11 and the patch 12.

The top release liner 13 is releasably attached to the underlying transdermal patch 12 as in the first embodiment. For example, the top release liner 13 is attached to the backing layer 12a by including an adhesive layer 16 between the top release liner 13 and the backing layer 12a, or by thermobonding the top release liner to the backing layer. However, in this embodiment the top release liner 13 has two tab regions 13a and 13b. First tab 13a extends partially over the patch 12 and extends partially beyond a first end margin 14 of the patch 12. Second tab region 13b may extend partially over the patch 12 and may, or may not, extend beyond a second end margin 15 of the patch. There is no need for both of the tab regions 13a and 13b to extend beyond end margins of the patch in this embodiment, because the top release liner is not removed by grasping a second tab in this embodiment. In this embodiment, if both tabs 13a and 13b extend over an end margin of the patch, the patch and top release liner may be removed from the bottom release liner 11 by grasping either extended portion of the tab. If only the first tab 13a extends over an end margin of the patch 12, then the first and second tabs may be differently and distinctly marked to aid a patch user in removing the patch from bottom release liner, as in the first embodiment.

In this embodiment, each tab 13a and 13b is releasably attached to the underlying patch 12 by means of adhesive layer 16 or by thermobonding. The adhesive layer 16 need not cover the entire area of the patch 12, but the adhesive must be sufficient to prevent the top release liner 13 from peeling when the top release liner and patch 12 are removed from the bottom release liner. As in the first embodiment, the ratio of the stripping load of the top release liner 13 from the backing layer 12a to the stripping load of the bottom release liner 11 from the patch 12 is preferably set to greater than or equal to 1.0 to prevent the top release liner 13 from peeling when the patch 12 is removed from the bottom release liner 11.

In this embodiment, a slit 17 separates the two tabs 13a and 13b. After removing the patch and top release liner 13 from the bottom release liner and then applying the patch to the skin or mucosa, the top release liner is removed by peeling back the tabs 13a and 13b. The tabs are removed by grasping the tab at the slit and then peeling back.

In this embodiment, a method used to remove the patch from the bottom release liner and then apply it to the skin or mucosa is similar to the method described for the first embodiment, except that the tabs are peeled back from the slit instead of pulling on the second tab.

Figure 5:
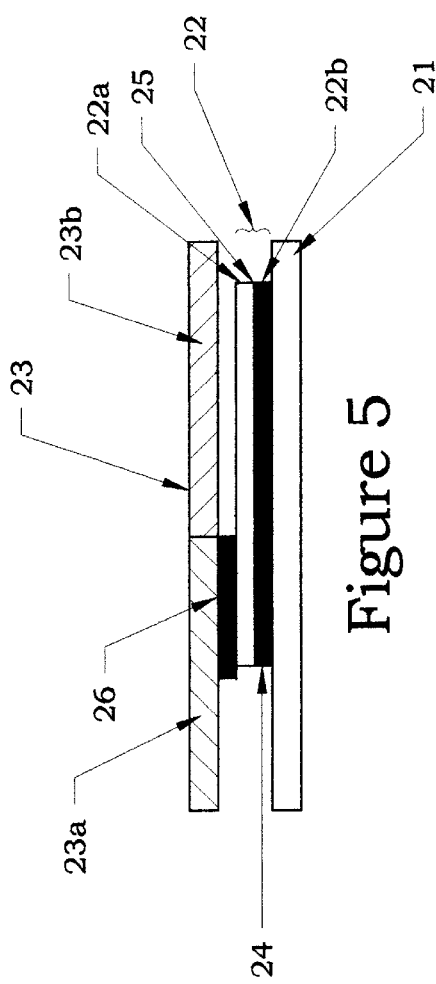
FIG. 5 is a side view of a third embodiment of the invention.
Figure 6:
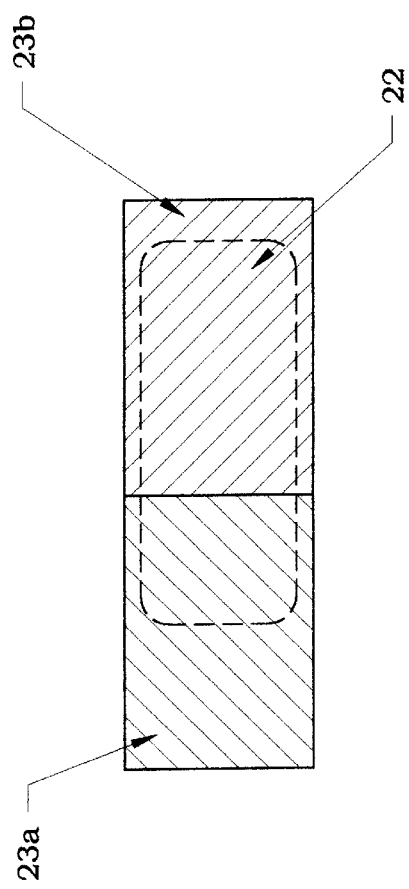
FIG. 6 is a top view of a third embodiment of the invention.

FIGS. 5 and 6 show a third embodiment of the invention. The third embodiment is similar to the first embodiment, but there is no central region of the top release liner in the third embodiment. Instead, in the third embodiment, the first tab 23a contacts the second tab 23b as seen in FIGS. 3a and 3b. However, like the first embodiment, the patch applicator of the third embodiment has a top release liner 23 with a first tab 23a and a second tab 23b, an adhesive layer 26, a transdermal patch 22 with a backing layer 22a and a patch adhesive layer 22b, and a bottom release liner 21.

While the invention may be practiced with a transdermal patch of any size, it is particularly advantageous with patches having a surface area of no more than 20 cm$^2$, and optimally no more than 10 cm$^2$.

Although the invention has been described and illustrated with respect to certain preferred embodiments, it should be understood that the description is for illustration and example only, and is not meant to limit the spirit and scope of this invention.

What is claimed is:

1. A transdermal patch applicator comprising:
   a bottom release liner;
   a transdermal patch releasably affixed to the bottom release liner; a top release liner releasably affixed to the transdermal patch, where the top release liner comprises at least one section and having a first tab, with at least a portion of the first tab extending beyond a first end margin of the transderrnal patch, and a second tab, with the second tab extending at least to a second end margin of the transdermal patch, and wherein said first tab facilitates removal of said release liner and said second tab facilitates removal of said top release liner from said transdermal patch.

2. The transdermal patch applicator of claim 1, wherein the top release liner has a second tab opposite to the first tab, and wherein the second tab extends partially over the transdermal patch and partially beyond the second end margin.

3. The transdermal patch applicator of claim 2, wherein the top release liner further comprises a central region between the first tab and the second tab, where the top release liner is releasably affixed to the transdermal patch only at the central region.

4. The transdermal patch applicator according to claim 1, where the top release liner has a second tab adjacent to the first tab, where the first tab and second tab are separated by a slit.

5. The transdermal patch applicator according to claim 1, where the surface area of the transdermal patch is 20 cm$^2$ or less.

6. The transdermal patch applicator according to claim 1, where the transdermal patch comprises a patch adhesive layer contacting the bottom release liner and a backing layer on the patch adhesive layer.

7. The transdermal patch applicator according to claim 6, where a ratio of a stripping load of the top release liner from the backing layer to a stripping load of the bottom release liner from the transdermal patch is greater than or equal to 1.0.

8. The transdermal patch applicator according to claim 6, where the patch adhesive layer comprises a drug.

9. The transdermal patch applicator according to claim 6, further comprising:

an adhesive layer between the top release liner and the backing layer.

10. The transdermal patch applicator according to claim 9, where the adhesive layer extends to a point directly over or slightly beyond the first end margin.

11. The transdermal patch applicator according to claim 6, further comprising:

a thermobond between the top release liner and the backing layer.

12. The transdermal patch applicator according to claim 2, where the first tab comprises a first identifying indicia, and the second tab comprises a second identifying indicia distinct from the first identifying indicia to aid in distinguishing the first and second tabs when applying the transdermal patch.

13. The transdermal patch applicator according to claim 12, where the first identifying indicia is a first color and the second identifying indicia is a second color.

14. The transdermal patch applicator according to claim 12, where the first identifying indicia is a first number and the second identifying indicia is a second number.

15. The transdermal patch applicator according to claim 1, where the first tab is over the bottom release liner, but not over the transdermal patch.

16. The transdermal patch applicator according to claim 1, where a ratio of a stripping load of the top release liner from the transdermal patch to a stripping load of the bottom release liner from the transdermal patch is greater than or equal to 1.0.

17. The transdermal patch applicator according to claim 2, where the second tab contacts the first tab.

18. The transdermal patch applicator according to claim 5, where the surface area of the transdermal patch is 10 cm$^2$ or less.

19. A method of applying a transdermal patch comprising the steps of: providing a transdermal patch applicator comprising a bottom release liner, a transdermal patch releasably affixed to the bottom release liner, a top release liner releasably affixed to the transdermal patch, wherein said the top release liner has a first tab, at least a portion of the first tab extending beyond a first end margin of the transdermal patch, wherein the first tab facilitates removal of the top release liner and the transdermal patch from the bottom release liner, and a second tab, at least a portion of the second tab extending beyond a second end margin of the transdermal patch, wherein the second tab facilitates removal of the top release liner from the transdermal patch;

pulling the first tab to remove the top release liner and the transdennal patch from the bottom release liner;

applying the transdermal patch to a patient's skin or mucosal surface;

pulling the second tab to remove the top release liner from the transdermal patch.

20. A transdermal patch comprising:

a bottom release liner;

a transdermal patch including a backing layer and an adhesive layer, said adhesive layer covering said backing layer and including a therapeutically effective amount of a drug for transdermal administration to a patient, a top release liner releasably affixed to the transdermal patch, wherein the top release liner has a first tab, at least a portion of the first tab extending beyond a first end margin of the transdermal patch, wherein the first tab facilitates removal of the top release liner and the transdermal patch from the bottom release liner.

21. The transdermal patch according to claim 20, wherein said top release liner has at least two sections, with said at least two sections having different physical characteristics.

22. The transdermal patch according to claim 20, wherein said at least two sections are made of different materials.

23. The transdermal patch according to claim 22, wherein said at least two sections have different thicknesses.

24. A transdermal patch applicator comprising:

a bottom release liner; a transdermal patch releasably affixed to the bottom release liner, the transdermal patch having a small surface area to avoid wrinkling of the transdermal patch during application;

a top release liner releasably affixed to the transdermal patch, wherein the top release liner has a first tab, at least a portion of the first tab extending beyond a first end margin of the transdermal patch, wherein the first tab facilitates removal of the top release liner and the transdermal patch from the bottom release liner.

* * * * *